United States Patent [19]
Grudzien, Jr. et al.

[11] Patent Number: 5,347,851
[45] Date of Patent: * Sep. 20, 1994

[54] CAPILLARY RHEOMETER PLUNGER PRESSURE TRANSDUCER AND MEASUREMENT TECHNIQUE

[75] Inventors: Christopher P. Grudzien, Jr., Mansfield, Mass.; Robert Malloy, Londonberry, N.H.; James F. Reilly, Shillington, Pa.

[73] Assignee: Dynisco, Inc., Sharon, Mass.

[ * ] Notice: The portion of the term of this patent subsequent to May 11, 2010 has been disclaimed.

[21] Appl. No.: 977,544

[22] Filed: Nov. 17, 1992

Related U.S. Application Data

[63] Continuation-in-part of Ser. No. 680,561, Apr. 4, 1991, Pat. No. 5,209,107.

[51] Int. Cl.$^5$ ............................................. G01N 25/00
[52] U.S. Cl. ....................................... 73/53.01; 374/56
[58] Field of Search ............... 73/53.01, 54.01, 54.02, 73/54.04, 54.07, 54.09, 54.11, 54.13, 54.14; 374/55, 51, 56

[56] References Cited

U.S. PATENT DOCUMENTS

| | | | |
|---|---|---|---|
| 2,487,161 | 11/1949 | Melton | 219/521 |
| 3,203,225 | 8/1965 | Sieglaff et al. | 73/54.14 |
| 3,270,553 | 9/1966 | Ballman et al. | 73/54.14 |
| 3,349,623 | 10/1967 | Paston | 73/726 |
| 3,758,776 | 9/1973 | Frohne et al. | 73/54.14 |
| 3,930,403 | 1/1976 | Cross et al. | 73/54.07 |
| 4,313,339 | 2/1982 | Nichols et al. | 73/54.14 |
| 4,539,837 | 9/1985 | Barnaby | 73/54.09 |
| 4,680,958 | 7/1987 | Ruelle et al. | 73/54.14 |
| 4,837,776 | 6/1989 | Poll | 374/56 |
| 5,127,269 | 7/1992 | Grudzien, Jr. | 73/705 |
| 5,209,107 | 5/1993 | Grudzien, Jr. et al. | 73/54.14 |

FOREIGN PATENT DOCUMENTS

| | | |
|---|---|---|
| 2317322 | 10/1974 | European Pat. Off. . |
| 275825 | 7/1988 | European Pat. Off. . |
| 455241 | 11/1991 | European Pat. Off. . |
| 57-045430 | 3/1982 | Japan . |
| 4307360 | 10/1992 | Japan . |
| 939535 | 10/1963 | United Kingdom . |
| 2164160 | 8/1984 | United Kingdom . |

OTHER PUBLICATIONS

"A simple capillary viscometer", C. Bowlt, Physics Education, vol. 10, No. 2, pp. 102–104, Mar., 1975.
"High-Pressure Capillary Viscometer (Exchange of Experience)", A. A. Bogatov, A. V. Serebryakov and V. I, Selivanov, Ural Polytechnical Institute, Sverdlovsk, vol. 57, No. 2, pp. 50–51, Feb., 1991.

*Primary Examiner*—Hezrone E. Williams
*Assistant Examiner*—Michael Brock
*Attorney, Agent, or Firm*—Wolf, Greenfield & Sacks

[57] ABSTRACT

A capillary rheometer apparatus includes a housing, a plunger, the housing having a reservoir for receiving the plunger in a polymer melt, and a mechanism for blocking flow of the melt out of the reservoir. A driving mechanism is included for driving the plunger longitudinally within the reservoir to move one end of the plunger in contact with the melt. A diaphragm, which is coupled to the one end of the plunger, deflects in response to melt pressure in the reservoir. A mechanism, responsive to diaphragm deflection, determines pressure of the melt. Another mechanism is included for determining the temperature of the melt and a further mechanism is included for indicating longitudinal movement of the plunger. From such determinations, the PVT characteristics and the apparent shear viscosity characteristics of the polymer melt can be obtained.

22 Claims, 11 Drawing Sheets

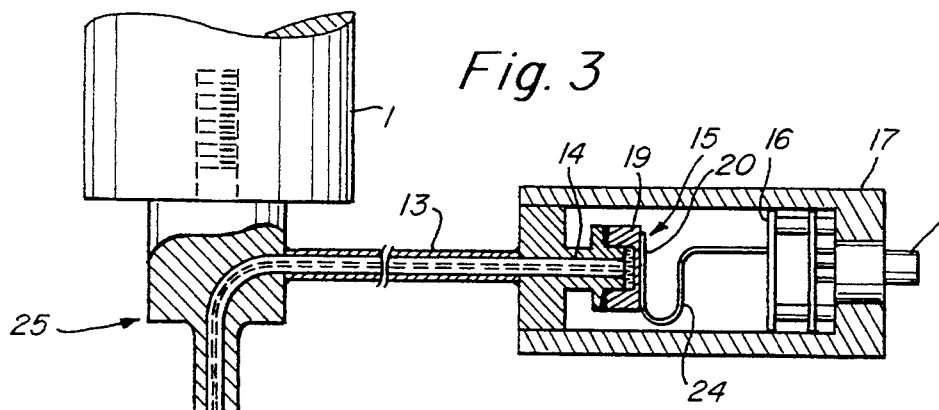
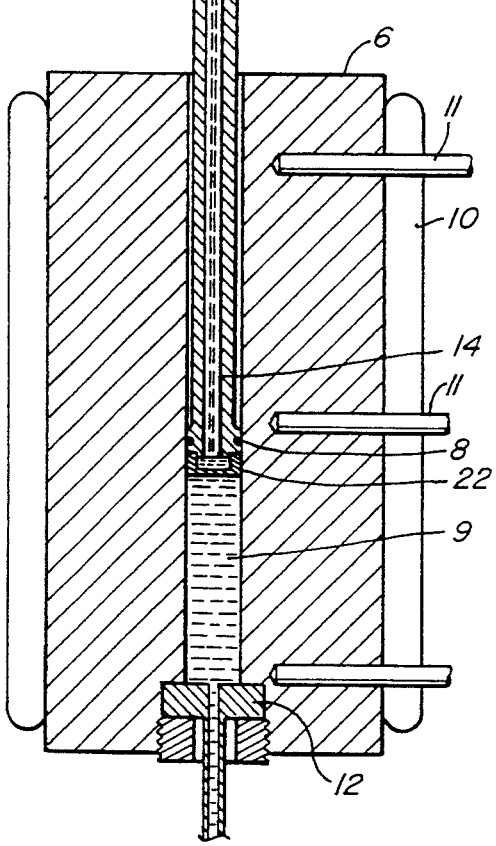
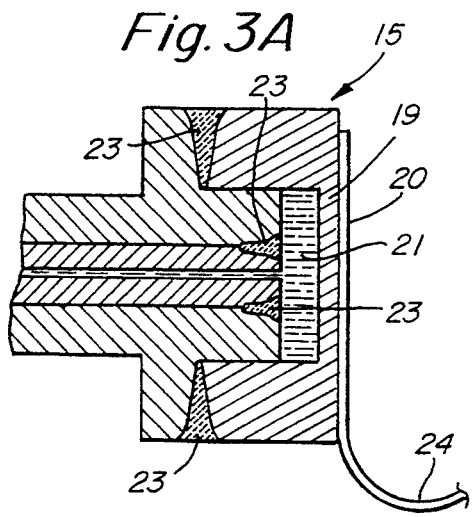
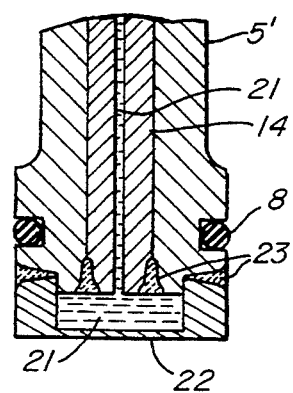

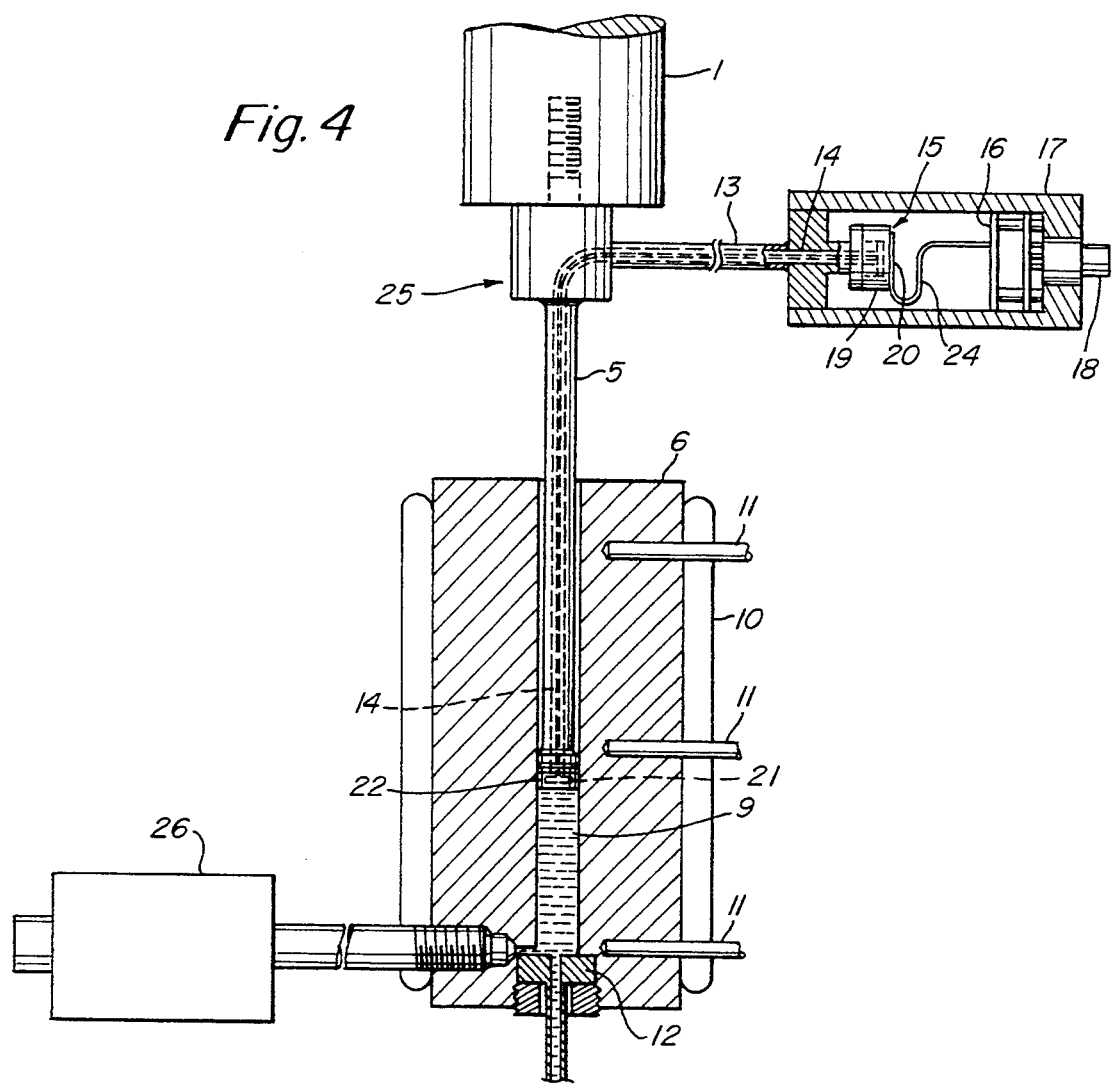

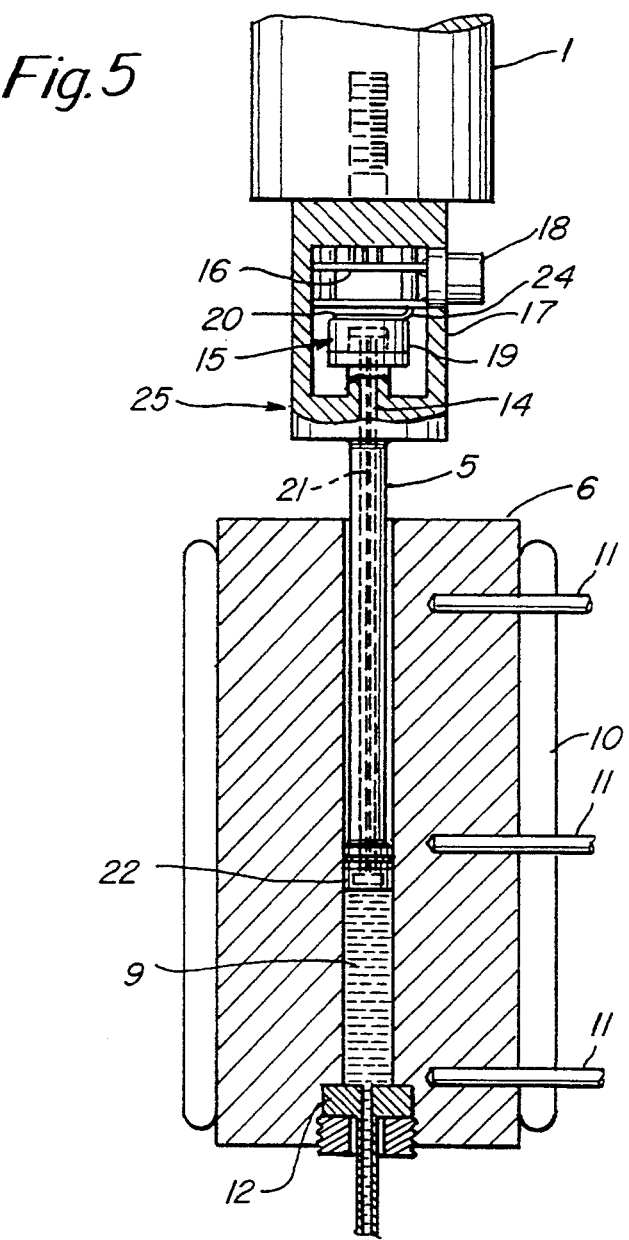

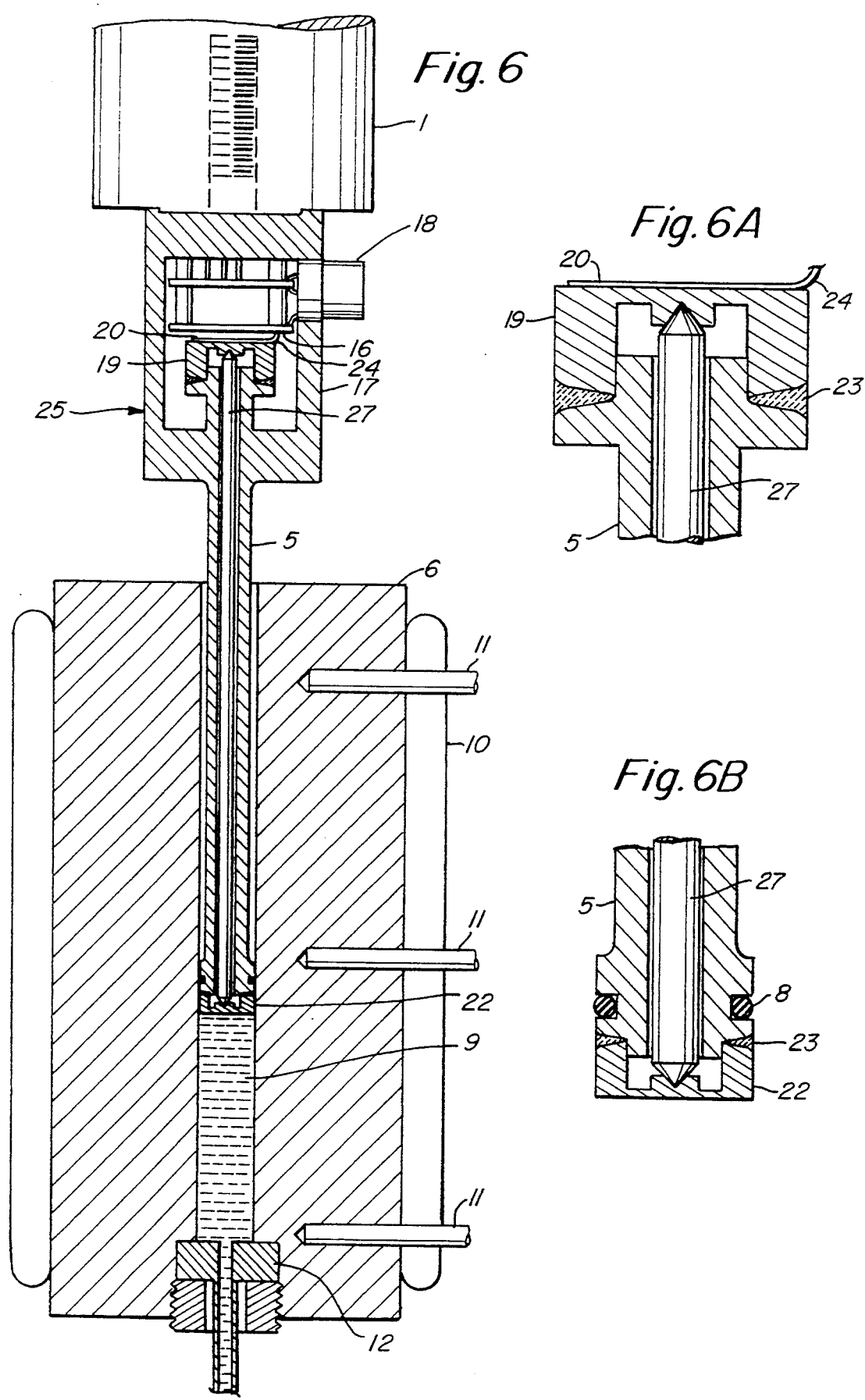

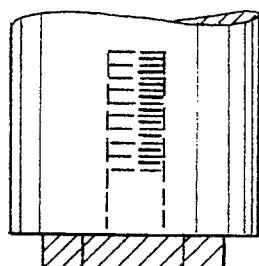
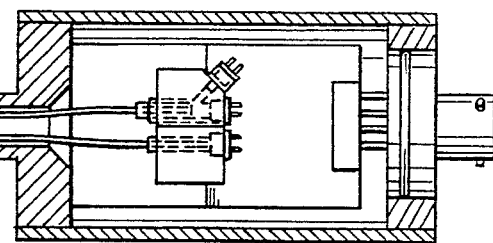
Fig. 10
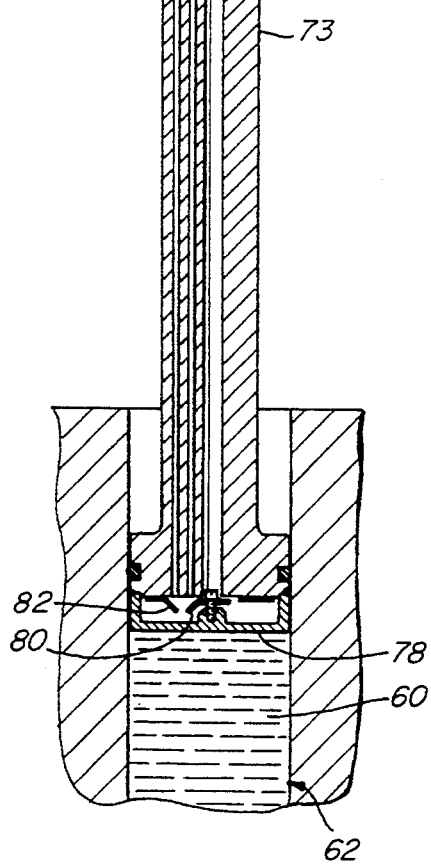
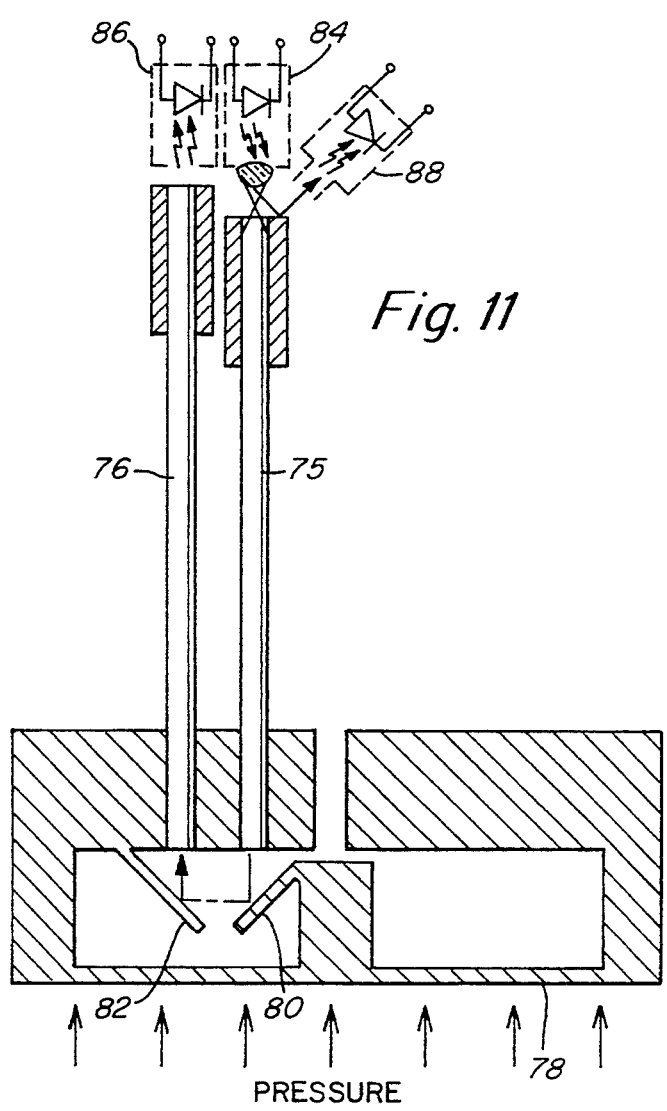
Fig. 11

CAPILLARY RHEOMETER PLUNGER PRESSURE TRANSDUCER AND MEASUREMENT TECHNIQUE

RELATED APPLICATION

This application is a continuation-in-part application under 35 U.S.C. §120 of application Ser. No. 07/680,561 filed Apr. 4, 1991, now U.S. Pat. No. 5,209,107, entitled "CAPILLARY RHEOMETER PLUNGER PRESSURE TRANSDUCER AND MEASUREMENT TECHNIQUE".

BACKGROUND OF THE INVENTION

1. Field of the Invention

The present invention relates to a capillary rheometer for establishing compressibility material properties and pertains, more particularly, to a capillary rheometer which utilizes a pressure measurement plunger for such purposes.

2. Background

Various types of capillary rheometers are utilized in the polymer industry to establish shear and temperature related material properties as well as compressibility properties. The theory of operation and design specifications for capillary rheometers are documented in U.S. Pat. No. 3,203,225.

Capillary rheometers generally operate by using a piston or plunger to force melted polymers, that have been heated in a barrel passage, through a capillary die. The force based plunger-barrel capillary rheometer utilizes a force sensor to measure the load or force applied to the plunger and a displacement sensor to measure the plunger velocity (displacement/unit time) through the stationary barrel. The apparent shear viscosity of the melted polymer can be determined using known relationships for flow of polymer melts through the cylindrical or other commonly used geometries. For example, wide thin slits or annulus geometries may be used. The apparent shear viscosity of a polymer melt at a given melt temperature is determined using the ratio of wall shear stress divided by apparent wall shear rate, for the capillary of a defined geometry. The wall shear stress depends upon the plunger force measured by the force sensor.

In addition to establishing shear and temperature related material properties, capillary rheometers can be modified to generate information on the compressibility of polymer melts. In such an application, the pressure-volume-temperature (PVT) relationships, so called "equation of state" relationships, of a polymer melt can be determined using the capillary rheometer in the following manner. The rheometer barrel is heated to a desired temperature in which polymer granules, pellets or powder are loaded into the barrel and allowed to soften due to the heat. A plunger is used to apply various levels of pressure to the polymer via weights, air pressure, mechanical pressure, or hydraulic pressure. A known diameter plunger with a force measuring sensor is used to determine the pressure within the polymer melt. The temperature of the polymer melt, and the volume of the polymer melt are determined as a function of applied pressure. The specific volume of the polymer, at various pressures, is plotted against polymer temperature to describe the PVT behavior of the polymer.

There are, however, a number of errors associated with the melted polymer apparent viscosity data and compressibility data determined using the above mentioned method. With respect to viscosity measurements, the shear stress and the apparent shear rate values have errors associated therewith. These errors will be described, in particular, with reference to a prior art embodiment of the present invention, as illustrated in FIGS. 1 and 2.

Shear stress values will be in error if determined by means of a force sensor, because the force at the top of the plunger is influenced by the following factors which are not considered when the force sensor method is employed:

1. The Pressure Drop in the Barrel: The barrel 6 of the capillary rheometer is itself a capillary of given diameter and continuously decreasing effective length as the plunger 5 moves downward. The force required to maintain flow through the barrel 6 (i.e., pressure drop along barrel 6) can be significant, especially since the shear rate associated with barrel flow is low, and melted polymers have relatively high viscosities at low shear rates as most polymers are pseudoplastic in nature. The pressure drop is not considered by the force sensor measurement and thus a resulting error occurs in capillary wall shear stress since the stress value calculated assumes all of the pressure drop is due to the capillary itself. In addition, this error is not a "constant" at a given temperature and plunger 5 speed since the effective length of the barrel 6 changes continuously.

2. Friction Between Plunger and Reservoir Wall: In order to minimize the flow of material back across the land of the plunger 5, the plunger 5 must be fitted tightly within the barrel 6. The plunger 5 may be relieved some distance back from the melted polymer 9 interface, although enough tightly fitted land must remain to (i) limit the back flow of melted polymer 9 and (ii) align the tip of the plunger 5 in the barrel 6. Low coefficient of friction plunger seals 8 are often used to reduce the back flow of the melted polymer 9.

The melted polymer 9 may stick to the wall of the barrel and may be sheared between the wall and the plunger 5 as the plunger 5 moves. The plunger 5 itself will rub against the barrel 6 wall unless it is perfectly straight, properly aligned, and has the correct dimensions. High pressures in the barrel 6, such as those encountered when working with viscous materials at high flow rates, could cause buckling of the plunger 5 within the barrel 6, and binding between the plunger 5 and barrel 6. The dimensions of both the plunger 5 tip and barrel 6 will also change when the operating temperature is changed. Changes in operating temperatures could result in scoring of the barrel 6, or the opening (or closing) of the gap through which back flow can occur due to thermal expansion differences between the plunger and the barrel. Therefore, plunger friction errors are likely to occur.

Plunger 5 friction errors are typically estimated by removing the capillary 12 and measuring the force required to force melted polymer 9 from the barrel 6, and extrapolating this to force data to a zero barrel length. The method has been criticized since the friction errors vary with driving pressure and flow rate, and it is also time consuming.

3. End Errors: The entrance area of capillary 12 and barrel 6 exit area is a region where large stresses are developed due to the funneling of the melted polymer 9 as it emerges from the barrel reservoir, as well as region where these stresses relax to their limiting value which occurs some distance along the length of the capillary 12 tube.

The exit pressure for capillary 12 has also been shown to be somewhat greater than zero for viscoelastic polymers. The exit pressure is the result of recoverable elastic energy within the melted polymer 9, caused by flow induced orientation of the polymer molecules during deformation upstream of the capillary 12 exit. Purely viscous materials have exit pressures of zero.

The end errors can be minimized using dies having longer L/D ratios, since they are essentially constants at a given temperature and rate, being independent of capillary 12 length. It should be appreciated that the end errors are a constant and, therefore, become smaller on a percentage basis as the capillary length increases. The errors can be eliminated using the procedure of classical hydrodynamics of plotting the pressure drop measured over a system containing both an entrance region and straight capillary 12 versus the L/R of the tube, for tubes of various lengths and constant diameter at each flow (or shear) rate. Extrapolation to a pressure drop at zero length gives the end effect in terms of absolute pressure. Extrapolation to zero pressure gives the end effect in terms of tube radii. An alternative method is to use a flow geometry, such as a wide thin slit, for which the pressure drop within the rheometric region of the flow can be measured directly.

4. Temperature and Compressibility: It is generally assumed that the temperature of the melted polymer 9 is constant, and that the melted polymer 9 is incompressible. Melted polymers 9 are in fact, however, compressible, and are generally viscous materials, having relatively low thermal diffusitivities, indicating that the temperature of the polymer is likely to increase as it progresses through the measurement system due to viscous dissipation, to a degree depending on conductive heat loss. In order to minimize viscous heating and compressibility effects, short L/D capillaries 12 are recommended, provided end errors and barrel 6 related errors can be accounted for, since their relative effect is more significant for shorter capillaries 12.

5. Elastic Distortion: Elastic distortion of the barrel and polymer viscosity both change with temperature and pressure, plunger velocity, alignment and force. These changes as well as seal quality affect the calculation of effective area used to determine the pressure generated within the barrel of the capillary rheometer. The exact magnitude of these errors in a capillary rheometer are unknown although elastic distortion and effective area calculations are well documented for dead weight piston gages.

The force/sensor pressure calculation does not take into consideration the clearance area between the plunger 5 and the inner barrel wall. The elastic distortion of the barrel and polymer viscosity change with temperature and pressure and plunger velocity. These unaccounted for changes cause errors in effective area and other related calculations.

6. Polymer Backflow/Leakage/Shear Rate Errors: The rate at which melted polymer 9 flows through the capillary 12 is assumed to be equivalent to the value determined using the distance swept by the plunger 5 per unit time, assuming incompressibility and mass conservation. There will however be some leakage of material across the land of the plunger 5, since the pressure on the melted polymer 9 is greater than atmospheric. The amount of back flow will be determined by the quality of the plunger seal 8. Close, tight tolerances between the barrel 6 and plunger 5 will reduce leakage. An increase in the land length (contact area) will also reduce leakage. However, an increase in the number of plunger seals 8, or in the contact area between the plunger 5 and barrel 6, is also expected to increase the magnitude of the plunger 5 barrel 6 friction force errors.

Force sensor pressure calculations do not take into consideration some leakage of the melted polymer across the plunger. There is, however, some leakage of the melted polymer across the plunger. Thus, errors are associated with this calculation. By increasing the number of plunger seals or the contact area between the plunger and inner barrel wall, while it reduces the leakage, it increases the friction errors.

Accordingly, it is an object of the present invention to provide an improved capillary rheometer which eliminates the need for a force based measurement plunger.

It is another object of the present invention to provide a capillary rheometer in which accurate shear stress and apparent shear rate values for a melted polymer can be determined.

It is another object of the present invention to provide a capillary rheometer in which accurate compressibility data for a melted polymer can be determined.

It is another object of the present invention to provide a capillary rheometer which will eliminate the need for corrective methods to account for errors due to the barrel pressure drop, friction between the plunger and inner barrel wall, end errors, temperature and compressibility errors, elastic distortion errors, leakage errors and other related errors.

It is another object of the present invention to provide a capillary rheometer which utilizes a pressure measurement plunger.

It is another object of the present invention to provide a capillary rheometer which utilizes a pressure sensor for sensing pressure exerted by the melted polymer.

SUMMARY OF THE INVENTION

To accomplish the foregoing objects, features and advantages of the present invention, there is provided a capillary rheometer apparatus which includes a housing, a plunger, the housing having a reservoir for receiving the plunger and a polymer melt, and means for blocking flow of the melt out of the reservoir. The rheometer further includes a driving mechanism for driving the plunger longitudinally within the reservoir to move one end of the plunger in contact with the melt. A diaphragm, which is coupled to the one end of the plunger, deflects in response to melt pressure in the reservoir. The rheometer further includes a mechanism, responsive to the diaphragm deflection, for determining pressure of the melt.

In one embodiment of the present invention, the melt pressure determining mechanism includes an optical sensing mechanism. In another embodiment of the present invention, the melt pressure detecting mechanism includes a coupler at the one end of the plunger and a liquid-filled capillary passage extending within the plunger.

The capillary rheometer further includes a mechanism for determining the temperature of the melt and a mechanism for indicating longitudinal movement of the plunger.

BRIEF DESCRIPTION OF THE DRAWING

Numerous other objects, features and advantages of the invention should now become apparent upon a reading of the following detail description taken in conjunction with the accompanying drawings, in which:

FIG. 3 is a cross-sectional view of the capillary rheometer of the present invention, illustrating use of the plunger pressure transducer assembly;

FIG. 3A is an exploded fragmentary view of the sensing diaphragm;

FIG. 3B is an exploded fragmentary view of the tip diaphragm;

FIG. 4 is a cross-sectional view of an alternate embodiment of the present invention illustrating the use of an additional pressure style transducer;

FIG. 5 is a cross-sectional view of an alternate embodiment of the present invention illustrating a liquid metal filled, rigid stem, capillary rheometer plunger transducer;

FIG. 6 is a cross-sectional view of an alternate embodiment of the present invention illustrating a push rod, rigid stem, capillary rheometer plunger transducer;

FIG. 6A is an enlarged, fragmentary, cross-sectional view of the push rod, rigid stem, plunger transducer of the capillary rheometer of FIG. 6;

FIG. 6B is an enlarged, fragmentary, cross-sectional view of the push rod, rigid stem, plunger transducer of the capillary rheometer of FIG. 6;

FIG. 10 is a cross-sectional view of an alternate embodiment of the present invention which utilizes a plunger pressure transducer assembly having an optical arrangement for sensing the pressure of the melted polymer;

FIG. 11 is a cross-sectional, partly schematic view of the optical sensing arrangement of FIG. 10.

DETAILED DESCRIPTION OF THE PREFERRED EMBODIMENT

In accordance with the present invention there is provided a capillary rheometer which utilizes a plunger pressure transducer assembly. This plunger pressure transducer assembly has a plunger with one end for forcing a melted polymer through a capillary and a diaphragm at the same end of the plunger for sensing the pressure in the polymer. It additionally has a capillary passage with a liquid metal fill fluid therein as well as another sensing diaphragm, located at the opposite end of the pressure transducer assembly from the plunger with a strain sensitive element bonded to the surface opposite the liquid metal fill. As the plunger is lowered and pressed onto the top of the melted polymer, generating a pressure internal to the melted polymer, the diaphragm at the tip of the plunger, nearest the melted polymer, deflects with the melted polymer pressure, and transmits this deflection to the liquid metal fill fluid in the plunger pressure transducer assembly. The other sensing diaphragm at the opposite end of the plunger pressure transducer assembly deflects with the pressure within the liquid metal fill fluid varying the resistance of the bonded strain sensitive element, yielding an accurate pressure measurement immune to any of the barrel friction related errors common to force based plunger measurement techniques.

Figure 1:
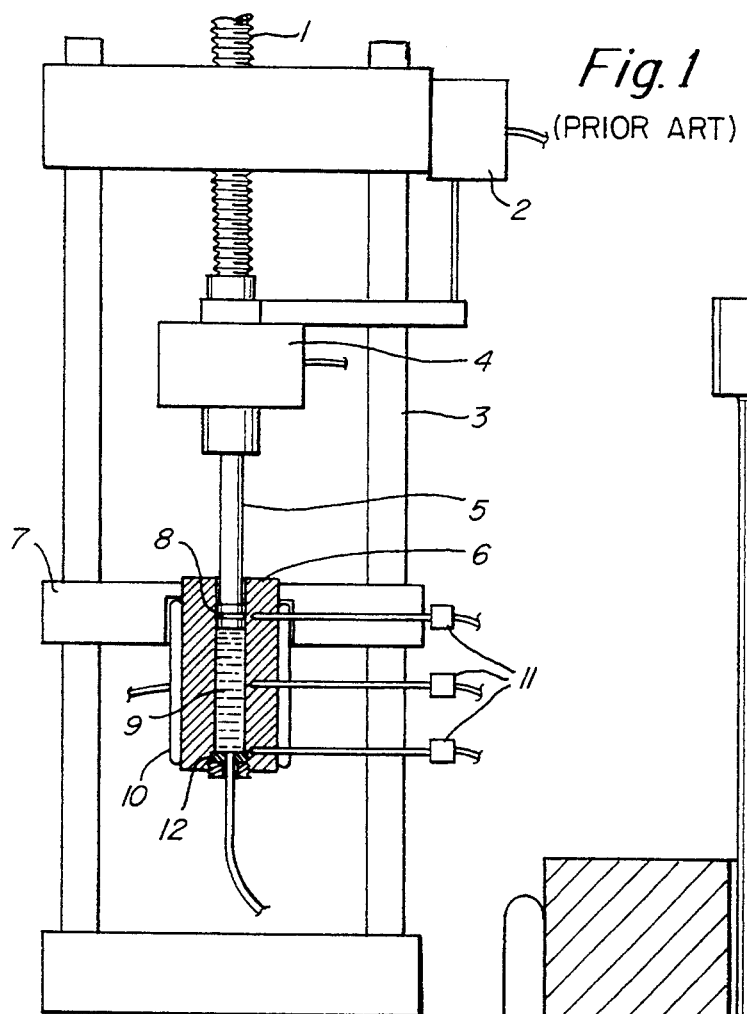
FIG. 1 is an elevational partially broken view of a prior art embodiment of a force based capillary rheometer including a force sensor.
Figure 2:
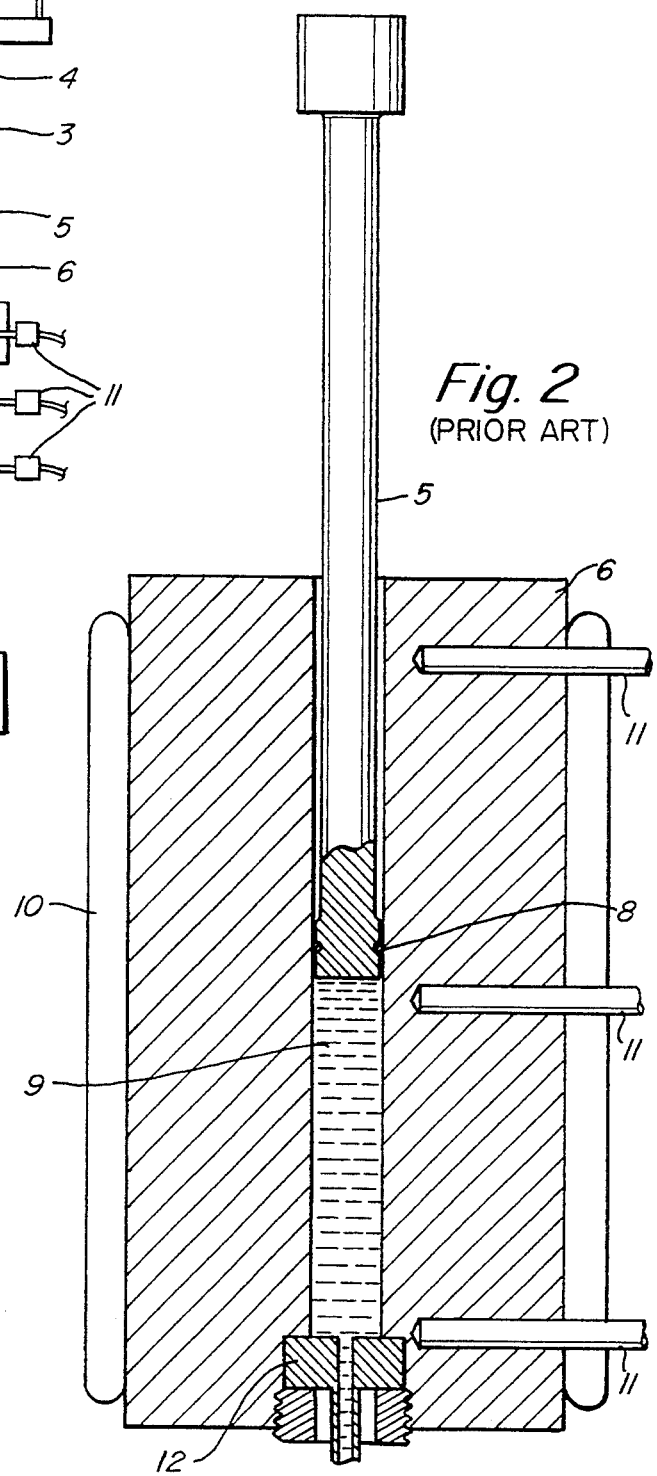
FIG. 2 is an enlarged cross-sectional view of the prior art force based capillary rheometer, illustrating in particular the force based plunger and the entrance to the capillary.

Reference is now made to the drawings and, in particular, to FIGS. 1 and 2 in which a prior art embodiment of the force based capillary rheometer is illustrated. A preferred embodiment of the present invention, illustrating the capillary rheometer with the pressure plunger transducer is shown FIG. 3. Alternate embodiments of the present invention, utilizing the plunger pressure transducer, are illustrated in FIGS. 4–11.

Figure 12:
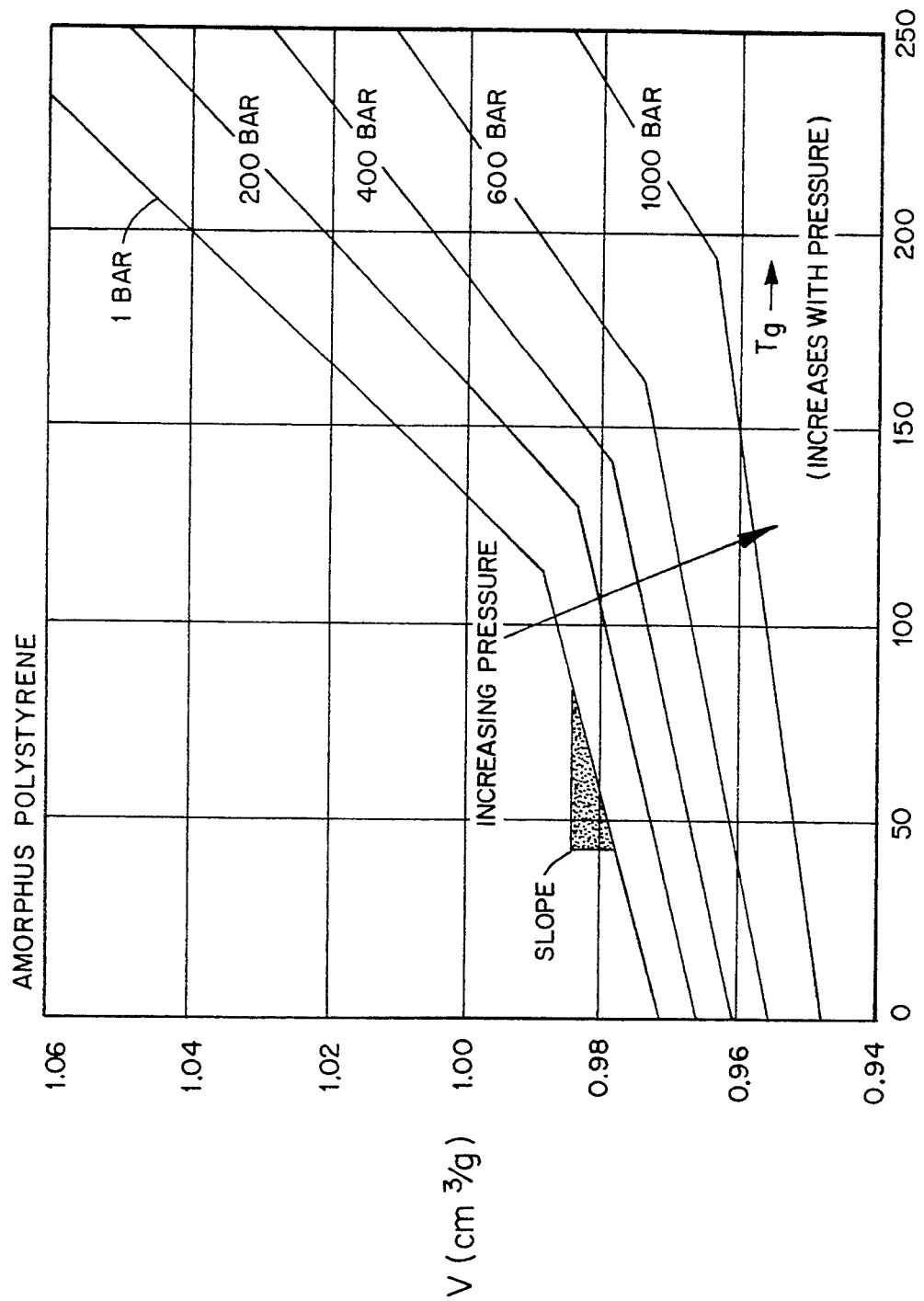
FIGS. 12 and 13 are curves illustrating the PVT behavior for certain typical polymers.
Figure 13:
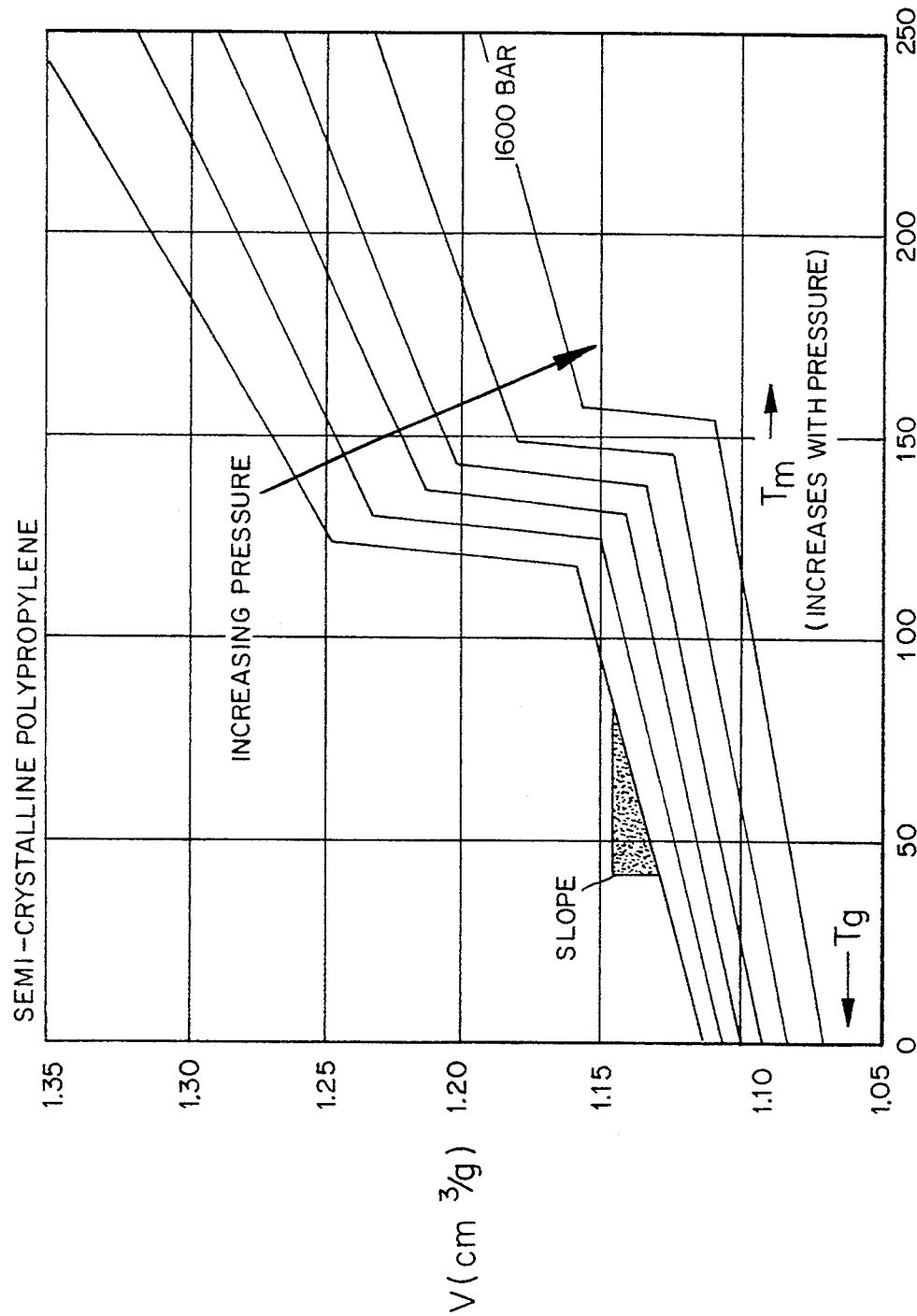

FIGS. 12 and 13 illustrate the pressure-volume-temperature characteristics of two different polymers.

Referring now in particular to FIGS. 1 and 2, which illustrate a standard force based type capillary rheometer, the force sensor 4 can be seen for measuring force of the plunger 5. Due to the aforementioned errors associated with this method, the present invention utilizes a pressure transducer assembly 25, replacing the force based measurement plunger, as illustrated in FIG. 3.

Force based plunger type capillary rheometers, as illustrated in FIGS. 1 and 2, use a piston or plunger 5 to force melted polymers, that have been heated in-situ, through a capillary die 12. The force, or melt pressure (calculated using the force measured by the force sensor 4 divided by the effective area of the plunger 5 required to maintain steady flow through the capillary die 12 at a given plunger velocity) is measured, and is indicative of the polymers' apparent shear viscosity.

The force based plunger-barrel capillary rheometer utilizes a force sensor 4 to measure the load applied to the plunger 5 in order to maintain a given plunger 5 velocity through the stationary barrel 6. The apparent shear viscosity of the melted polymer 9 can be determined using the relationships for flow of polymer melts through cylindrical geometries (i.e. pipe pressure flow). The apparent shear viscosity of the polymer melt at a given melt temperature and pressure, at the wall of the capillary 12, is determined by the ratio of wall shear stress divided by apparent wall shear rate, for the capillary 12 of defined geometry. The pressure gradient along the length of the capillary 12 is indicative of the shear stress. The discharge pressure of the capillary 12 is assumed to be zero, so the pressure gradient is the capillary 12 entrance pressure divided by the capillary 12 length. The apparent shear rate at the wall of the capillary 12 is calculated from the melted polymer 9 flow rate through the capillary 12, which is determined by monitoring the position of the piston by means of a displacement sensor 2 in the barrel with respect to time assuming melted polymer 9 incompressibility and mass balance.

Also illustrated in FIGS. 1 and 2 is the load screw 1 or the like which can be driven by electromechanical or servohydraulic/electromechanical, servohydraulic-pneumatic means, or using weights and the force of gravity. The problem with using weights, however, is that perfect alignment is necessary but difficult to achieve in practice, which in turn causes excessive friction error. In addition, the support columns 3 are shown for supporting the plunger 5 and barrel 6. In addition, a support bracket 7 is shown supporting the barrel 6 between the support columns 3. Also shown are the plunger seals 8 for containing the melted polymer 9 within the barrel 6. In addition, the heater 10 is shown for heating of the barrel 6, as well as temperature sensors 11 for temperature detection thereof.

The forced based plunger-barrel capillary rheometer may also be used to determine the compressibility of the melted polymer. Instead of using the piston or plunger 5 to force the melted polymer through a capillary die 12, a plug is used to maintain the melted polymer within the barrel 6. The compressibility of the polymer melt can be determined from the relationship between the pressure sensed and the plunger position.

The aforementioned errors associated with these force based capillary rheometers, however, render them inaccurate.

The present invention provides a capillary rheometer in which the aforementioned errors and corrective techniques are avoided. FIG. 3 illustrates a preferred embodiment of the capillary rheometer of the present invention in which a pressure transducer assembly plunger replaces the old force based measurement plunger. The capillary rheometer, as shown in FIG. 3, consists of a barrel 6 heated by an electrical power-controlled heater 10 with an appropriate capillary 12 retained at the bottom. The plunger 5 (as shown in FIG. 2) has been replaced by a plunger pressure transducer assembly 25. The plunger pressure transducer assembly 25 is moved downward by the motor, a dead weight, or a pneumatic, mechanical, or hydraulically driven drive head, in a controlled rate of descent or at a constant stress. It is to be appreciated that pneumatic rheometers typically employ a constant pressure rather than a constant speed as in the motorized type. The diaphragm 22 of the plunger pressure transducer assembly 25 presses onto the top of the melted polymer 9 generating a pressure internal to the melted polymer 9 and the liquid metal fill fluid 21, as will be described below. The plunger seal 8 prevents the melted polymer 9 from escaping around and past the plunger pressure transducer assembly 25 and out the top of the barrel 6 and the associated seal friction is not considered in the pressure measurement. Melted polymer 9 begins to flow through the capillary 12 in a calculable manner. The tip diaphragm 22 transmits the melted polymer pressure, in this configuration, to a fill liquid metal fluid 21 within the metal capillary 14 in the plunger pressure transducer assembly 25. The sensing diaphragm 19 deflects in response to the transmitted pressure of the liquid metal fluid 21, straining the four strain sensitive resistive elements within strain gage 20. The four strain sensitive resistive gage elements are arranged in a Wheatstone bridge configuration, with two increasing and two decreasing resistive elements. The strain induced resistive changes are then transformed into a voltage change. The voltage change is directly proportional to the pressure change in the Capillary Rheometer barrel 6 and inversely proportional to the voltage supplied to the Wheatstone bridge. Further details of the sensing diaphragm are illustrated in the exploded fragmentary of FIG. 3A. Similarly, further details of the tip diaphragm 22 are illustrated in the exploded fragmentary view of FIG. 3B.

In accordance with this preferred embodiment of the present invention, as illustrated in FIG. 3, further details of the plunger transducer assembly 25 will be described below. The metal capillary 14 can be seen within the metal armor flex hose 13 for flexible movement. The metal capillary 14 encloses the liquid metal fill fluid 21. Tube 14 is welded at 23 to plunger 5 and metal case 17 at its ends. Tube 14 is then filled and capped off with diaphragms 22 and welds 23. The measurement diaphragm assembly 15 acts to measure the pressure of the liquid metal fill fluid 21 within the metal capillary 14. The measurement diaphragm assembly 15 includes the temperature compensation printed circuit board assembly 16. Strand gage 20 is attached to circuit board 16 via flexible circuit board 24. This measurement diaphragm assembly 15 is enclosed in metal case 17. An electrical connector 18 is provided on the periphery of the metal case 17.

Figure 8:
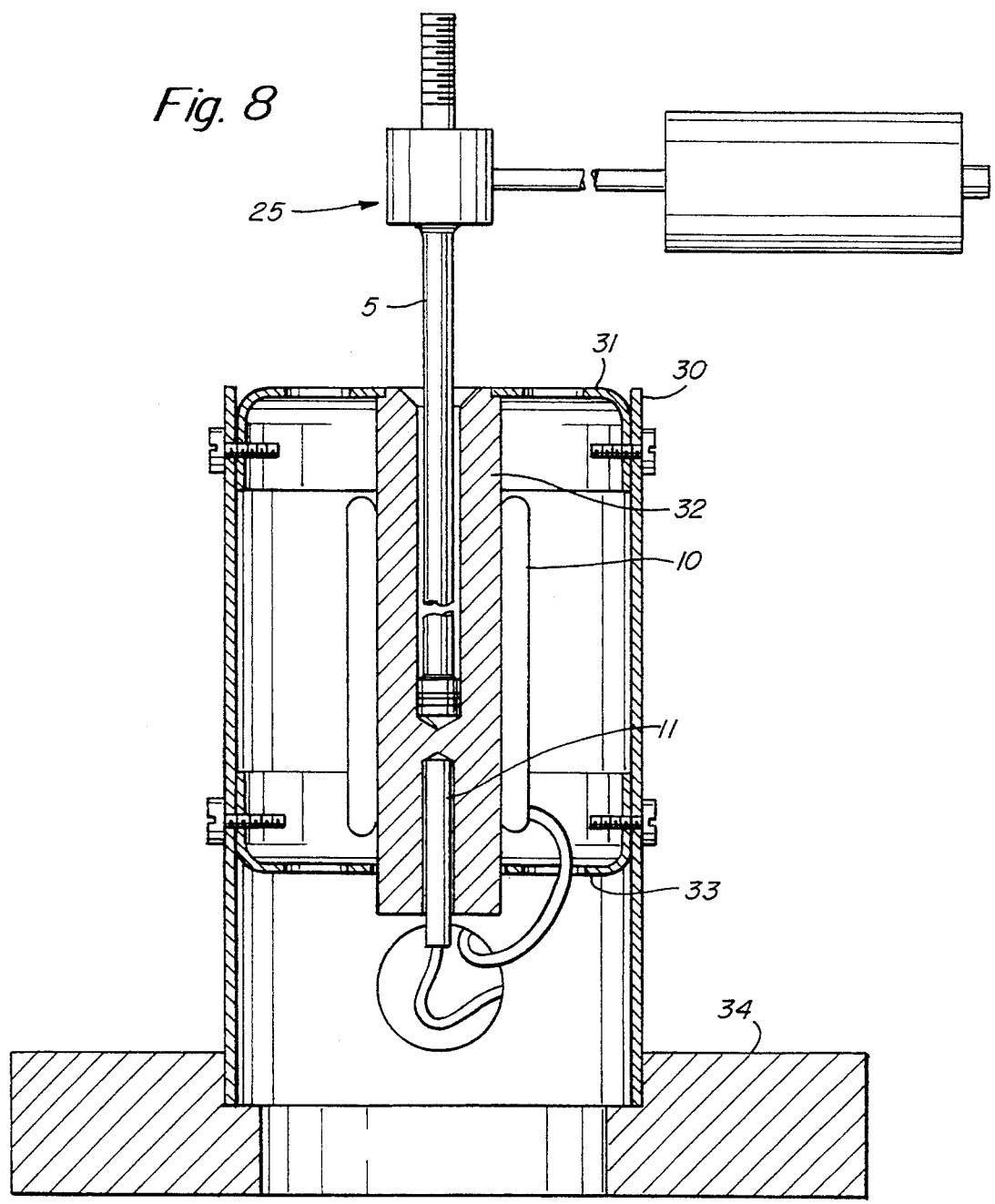
FIG. 8 is a cross-sectional view of an alternate embodiment of the present invention illustrating use of a heater block holder for the capillary rheometer plunger transducer.

In an alternate embodiment of the present invention, in order to maintain thermal stability and minimize temperature induced errors in the plunger transducer assembly 25 during operation with the capillary rheometer, a heater block holder is utilized, as illustrated in FIG. 8. The capillary rheometer plunger transducer rests within a holder 32, which is heated by an electrical heater 10 to the temperature of the polymer under test, measured by the temperature sensor 11 and controlled by a conventional temperature controller (not shown). The base 34 supports the outer cylindrical shell 30, which acts as a heat shield for the holder 32 and the heater 10. The upper 31 and lower 33 plates support and maintain centrality, respectively, of the holder 32 and provide a plenum for air circulation from the holes provided in the outer cylindrical shell 30 through to the lower 33 and upper 31 plates.

The plunger pressure transducer assembly 25 is placed in the holder 32 during purging, cleaning, reloading and packing of the polymer under test in the capillary rheometer. The plunger pressure transducer assembly 25 is removed from the holder 32, inserted into the capillary rheometer barrel 6 and allowed to thermally stabilize for a short period of time prior to testing. With the plunger pressure transducer assembly 25, pressure measurements are made as opposed to force based plungers with which force measurements are made. Thus, the implementation of a plunger transducer assembly 25 into a forced based type capillary rheometer, eliminates errors related to the seal frictional force component. In addition, the implementation of a plunger transducer assembly 25 into a forced based capillary rheometer eliminates the clearance area uncertainties from the pressure measurement calculations required to establish a polymeric material's shear viscosity. Better sealing can be achieved and therefore lower shear rate uncertainty achieved, since the improved sealed quality can be used with no influence on the measured pressure value.

The viscosity of the polymer in the barrel 6 of the capillary rheometer can be determined using the plunger transducer assembly 25 (i.e., the viscosity of the polymer at shear rates lower than those encountered in the primary capillary) if the difference between the plunger 5 and barrel 6 discharge pressure can be measured.

The addition of another melt pressure style transducer 26, as shown in FIG. 4 with a rheometer which utilizes a pressure transducer before the capillary die would allow the measurement of the pressure difference. It should be appreciated, however, that the use of the combination plunger/pressure transducer in conjunction with a rheometer which utilizes a pressure transducer before the capillary dye does not offer the advantages that it does when implemented in a standard force based capillary rheometer, since the barrel pressure drop or plunger friction errors are not encountered with this rheometer. The use of such a device, however, with the rheometer which utilizes a pressure transducer before the capillary die would allow one to evaluate viscosity at low barrel and high capillary shear rates at each plunger speed since the barrel itself can be considered a large diameter capillary.

Barrel reservoir pressure drop (or head effect) is one of the factors that contributes to the force reading for piston rheometers which utilize compressive load sensors at the upper end of the piston. The barrel pressure drop error is described as being significant. The existence of this error has in fact influenced certain rheological measurement practices.

Instruments such as an extrusion plastometer require that measurements must be made within certain piston height limits.

Development of piston rheometers which utilize pressure transducers at the entrance to the capillary die eliminate the pressure drop error because measurements are downstream from the barrel.

The barrel pressure drop is equivalent to:

$$\Delta P_B = \frac{8 Q_B \mu_B L_B}{\pi (R_B)^4}$$

where:
$Q_B$ = volume flow rate through the barrel
$\mu_B$ = viscosity of the material in the barrel
$R_B$ = radius of the barrel (inner)
$L_B$ = effective length of the barrel (the distance between the piston tip and capillary entrance).

while the capillary pressure drop is equivalent to:

$$\Delta P_C = \frac{8 Q_C \mu_C L_C}{\pi (R_C)^4}$$

where:
$Q_C$ = volume flow rate through the capillary
$\mu_C$ = viscosity of the material in the capillary
$L_C$ = length of the capillary
$R_C$ = radius of the capillary For a Newtonian, uncompressible fluid, the ratio of the barrel pressure drop to the capillary pressure drop (which is an indicator of the magnitude of the error) is equivalent to:

$$\frac{\Delta P_B}{\Delta P_C} = \left| \frac{R_C}{R_B} \right|^4 \times \left| \frac{L_B}{L_C} \right|$$

The error decreases as the test progresses because the effective length of the barrel decreases continuously throughout the test.

Most plastic materials are pseudoplastic in nature, having viscosities that decrease with increasing shear rate. For non-Newtonian materials, such as plastic melts, this ratio $$\frac{\Delta P_B}{\Delta P_C} = \frac{\mu_B L_B (R_C)^4}{\mu_C L_C (R_B)^4}$$

where $\mu_B > \mu_C$ and for highly pseudoplastic polymers, $\mu_B >> \mu_C$, since the shear rates in the larger diameter barrel are must lower than those in the typically smaller diameter capillary at the same volume flow rate. The barrel pressure drop error is, therefore, more significant for pseudoplastic materials (for a given rheometer and capillary geometry) than for Newtonian materials.

The alternate embodiment capillary rheometer, as shown in FIG. 4, utilizes two pressure transducers, one being integral to the plunger, the other being placed at the capillary die entry. The difference in the two pressure readings is the barrel pressure drop, $\Delta P_B$. Using this system, the apparent shear viscosity of the material in the barrel, and the viscosity of the material in the capillary (subject to the usual capillary end error correction) can be calculated simultaneously.

Barrel $$\mu_{a,B} = \left| \frac{\Delta P_B}{L_B} \right| \times \left| \frac{\pi (R_B)^4}{8Q} \right|$$

where
$\mu_{a,B}$ = apparent melt shear viscosity in the barrel at $$a,B = \frac{4Q}{\pi (R_B)^3}$$

apparent shear rate.
Q = volume flow rate, $R_B$ = barrel radius $$\frac{\Delta P}{\Delta L_B} = \frac{P_{(Piston-Pentrance)}}{(Effective\ Barrel\ Length)}$$ Dynamic but a "constant" at each Q Capillary $$\mu_{a,c} = \left| \frac{\Delta P_C}{L_C} \right| \times \left| \frac{(R_C)^4 \pi}{8Q} \right| \text{ at}$$

$\mu_{a,c}$ = apparent melt viscosity for the polymer
in the capillary die (higher shear date)

$$a,c = \frac{4Q}{\pi (R_C)^3}$$

$L_C$ = capillary length
$\Delta P_C$ = capillary pressure drop

The apparent melt viscosity of the polymer is determined at two shear rates for each plunger speed (flow rate) with this system. The melt flow characteristics of the polymer are evaluated over a wider range of shear rates than can be evaluated utilizing a conventional force based capillary rheometer.

Alternate embodiments of capillary rheometer utilizing plunger transducer assemblies are illustrated in FIGS. 5, 6 and 7 and 9.

FIG. 5 shows the implementation of a liquid metal filled, rigid stem, capillary rheometer plunger transducer. As can be seen in FIG. 5, the metal case 17, enclosing the measurement diaphragm assembly 15, is attached directly to the plunger 5, rather than from the interim metal armor flex hose 13. This alternate arrangement is thus referred to as a "rigid stem" system.

FIG. 6 shows the implementation of a push rod, rigid stem, capillary rheometer plunger transducer. As in FIG. 5, this system is a rigid stem system. The alternate embodiment of FIG. 6 also includes a push rod 27 within the plunger transducer assembly 25. The push rod 27 is indicated predominantly in FIG. 6.

Figure 7:
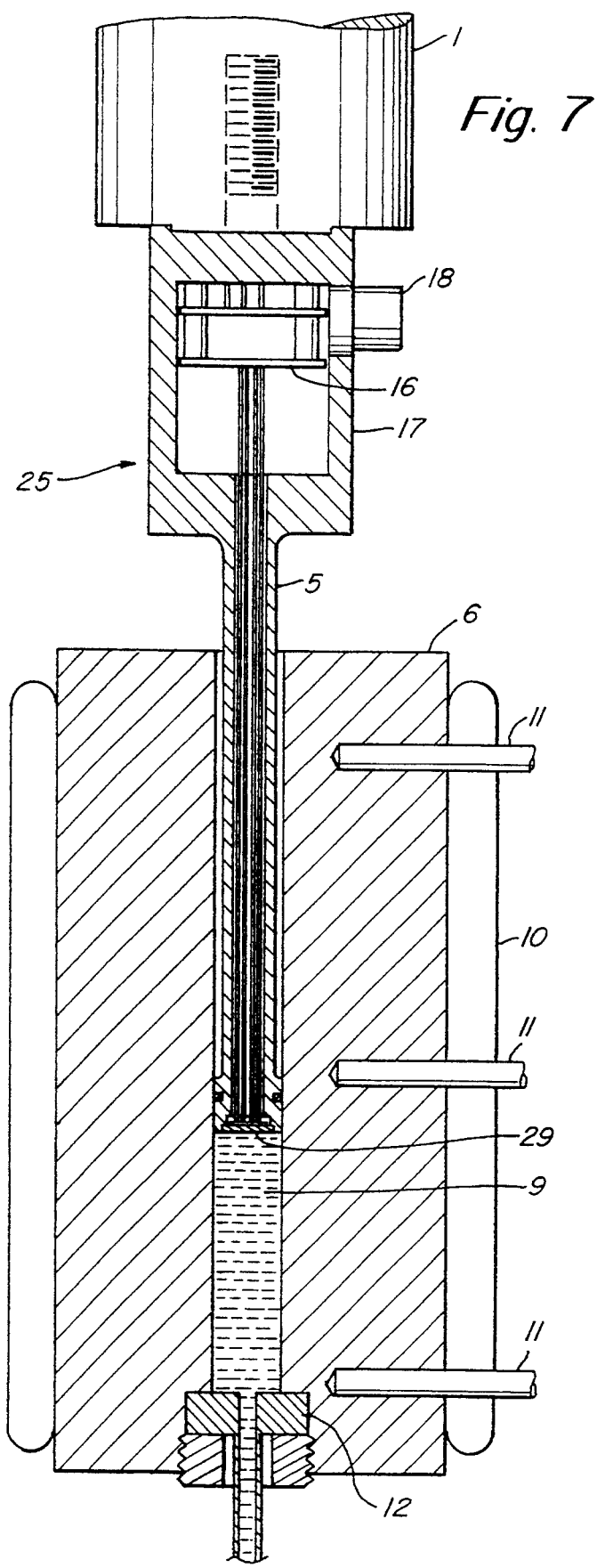
FIG. 7 is a cross-sectional view of an alternate embodiment of the present invention illustrating a non-bonded piezo resistive type, rigid stem, capillary rheometer plunger transducer.
Figure 7A:
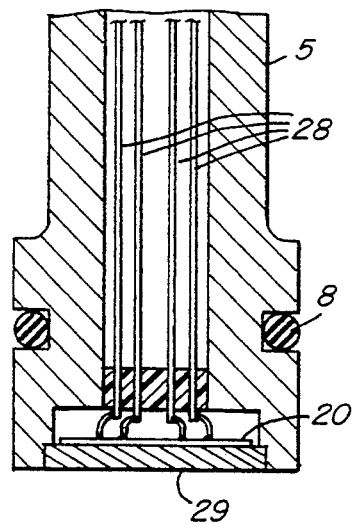
FIG. 7A is an enlarged, fragmentary, cross-sectional view of the non-bonded piezo resistive plunger transducer of the capillary rheometer of FIG. 7.

FIG. 7 shows the implementation of a non-bonded piezo resistive type, rigid stem, capillary rheometer plunger transducer. This alternate embodiment, like the embodiments in FIGS. 5 and 6, is a rigid stem system. The alternate embodiment in FIG. 7, however, includes a measurement diaphragm 29 consisting of either a highly elastic non-metallic monocrystalline structure or a polycrystalline structure. Also shown in FIG. 7 are the high-temperature electrical connections 28 for communication with the strain gage 20. Further details of the measurement diaphragm 29 and high-temperature electrical connections 28, which communicate with the strand gage 20, are illustrated in the enlarged, fragmentary, cross-section view of FIG. 7A.

Figure 9:
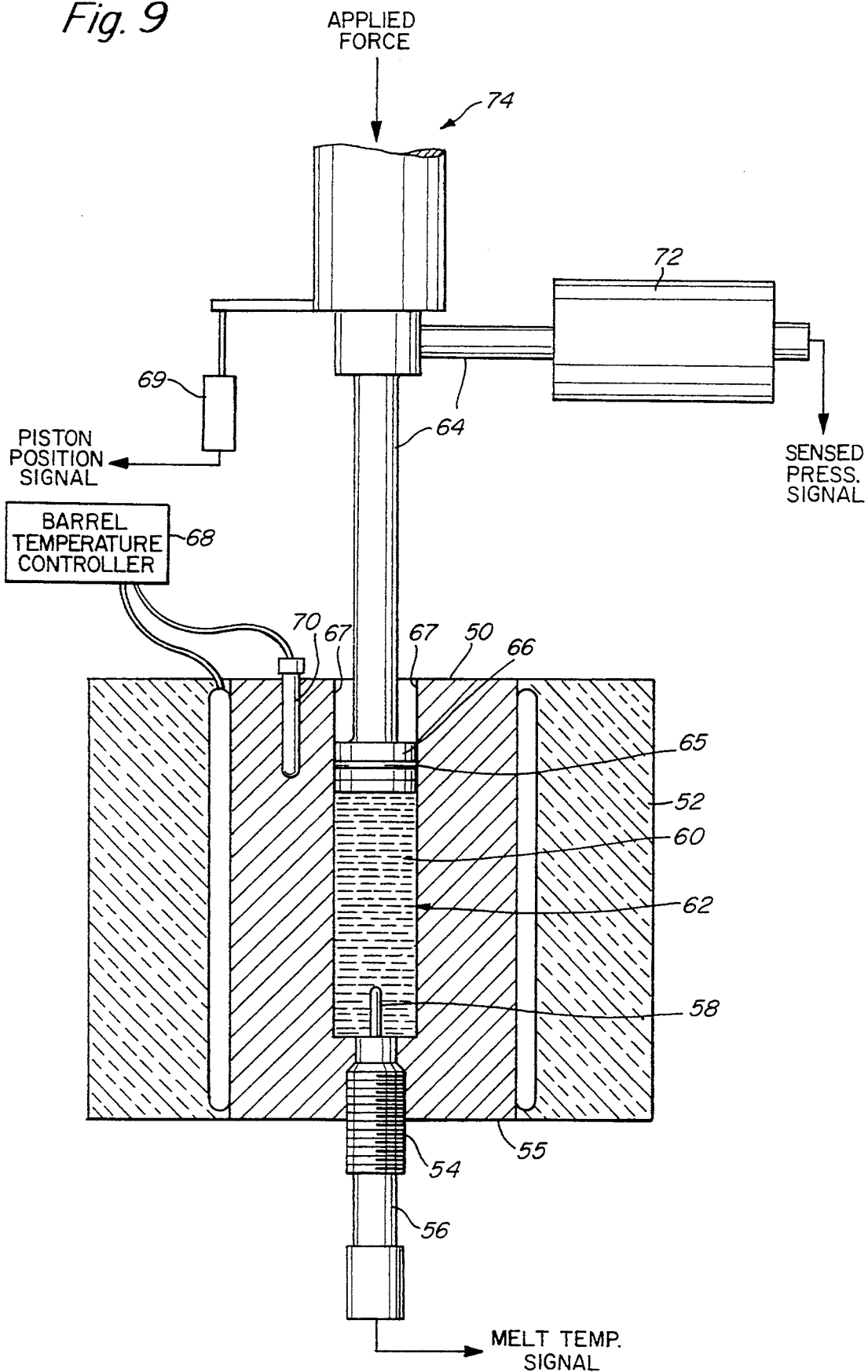
FIG. 9 is a cross-sectional view of an alternate embodiment of the present invention illustrating a PVT capillary rheometer apparatus which utilizes the plunger pressure transducer assembly.

FIG. 9 illustrates a capillary rheometer apparatus utilizing the plunger pressure transducer assembly of the present invention. A capillary rheometer can be used to determine the pressure-volume-temperature (PVT) behavior of a polymeric material. The material is placed in a temperature controlled chamber, allowed to reach thermal equilibrium, and the volume of the polymer in chamber is measured as pressure is applied to the polymer through an instrumented piston. The test procedures are repeated at various barrel temperatures and piston pressures. The specific volume of the polymer, at various pressures, is plotted against the polymer temperature to describe the PVT behavior of the polymer, as described below. As shown, in FIG. 9, an electrically heated stationary barrel 50 includes a polymer reservoir 62. Plug 54 is fixed to the lower portion 55 of barrel 50, which plugs the lower portion of reservoir 62. A predetermined mass of polymer granules, pellets, powder or liquid is loaded into the reservoir 62 within barrel 50. Barrel 50 is heated by barrel temperature controller 68 having probe 70, causing the polymer 60 to melt. A plunger pressure transducer assembly 64 includes an instrumented piston 66 and an integral pressure sensor 72. A high pressure seal 65 exists between the instrumented piston 66 and inner walls 67 of reservoir 62. Mechanism 74 is used to apply force to the top of the plunger pressure transducer assembly 64. Mechanism 74 may include a dead weight or electrically driven, hydraulically driven, or pneumatically driven load screw, or the like. The plunger pressure transducer assembly 64 applies, through the instrumented piston 66, pressure to the polymer melt 60 within reservoir 62. Plunger pressure transducer assembly position sensing device 69 senses the change in axial position of the piston 66. The position sensing device 69 may include an optical encoder or LVDT. Pressure sensor 72 senses the pressure applied to the polymer melt 60. Melt temperature sensor 56, including probe 58, senses the temperature of the polymer melt 60. Melt temperature sensor 56 may include an extended thermal couple RTD or an infrared transducer. In addition, as shown, the apparatus includes insulation 52 on the outer sides of barrel 50 to prevent the outer sides of the barrel from reaching extremely high temperatures. Once a desired pressure level is reached, the pressure is maintained until steady state conditions are reached with respect to temperature and position. The procedure is repeated at various desired temperatures and pressure levels and temperature, position and pressure results are recorded.

Based on the test results, the relationship between the polymer's melt temperature, pressure, and specific volume is established. Specific volume (volume/mass) at any given pressure and temperature is determined by comparing the change in volume (volume swept by the piston) to the volume at atmospheric pressure. The relationship between the polymer's volume, temperature and pressure (PVT behavior) determines the behavior of the polymer material and influences the quality of products obtained from a manufacturing process utilizing such polymer material, such as injection molding. A polymer's PVT behavior is typically characterized for either process design or material quality control purposes. Thus, a capillary rheometer apparatus which can accurately yield accurate PVT information, is desired.

The PVT relationship for a polymeric material is generally given by:

$$(p+\pi)(v-\beta)=RT$$

where:
p = melt pressure
$\pi$ = a material constant
v = specific volume of the melt (volume/mass)
$\beta$ = a material constant
R = universal gas constant
T = melt temperature The PVT behavior for a typical amorphous polymer such as polystyrene is illustrated in FIG. 12. FIG. 12 shows that the specific volume of an amorphous polymer increases with increasing temperature, and decreases with increasing pressure. The curve in FIG. 12 also shows that the rate of change of specific volume with temperature and pressure increases above the glass transition temperature ($T_g$) of the polymer.

The PVT behavior of a semi-crystalline polymer such as polypropylene is shown in FIG. 13. FIG. 13 also shows that the specific volume of such a polymer increases with increasing temperature, and decreases with increasing pressure. The PVT behavior of a semi-crystalline polymer differs from that of an amorphous polymer in that there is a major discontinuity in each specific volume vs. temperature curve (isobar) at the polymer's melting temperature ($T_m$).

The capillary rheometer apparatus of FIG. 9 can also be used in the unsteady state mode to evaluate the specific heat of a polymer by looking at the temperature increase associated with compression assuming adiabatic conditions (adiabatic heating or cooling during instantaneous pressure changes). Fast response melt temperature probes and low thermal conductivity barrels are desirable for such an evaluation to minimize heat loss. The adiabatic temperature rise is given by:

$$\Delta T = \Delta P / \rho C_p$$

where:

Δt = instantaneous melt temperature change
ΔP = pressure change
ρ = density
$C_p$ = specific heat at constant pressure The specific heat is calculated based upon the measured variables, ρ, ΔT, and ΔP.

Use of the plunger pressure transducer assembly in the capillary rheometer apparatus allows for direct measurement of both pressure and temperature along the center of the molten polymer within the reservoir. The direct pressure measurement is advantageous over indirect measurements which involve friction and leakage. The quality of the piston seal is particularly important in PVT applications since pressures are high (potentially up to 30,000 psi). Tight piston seals would result in high frictional forces. However, a stationary pressure sensor placed at the bottom of the barrel would work just as well, except that temperature could not properly be measured in that some location. It will be appreciated by those skilled in the art that pressures could be measured at right angles to the melt flow. This could be done (1) at the reservoir wall (which would change the volume of the reservoir since the sensor has a flat face) of (2) through an interconnecting hole (which would change the volume of the chamber of the reservoir and introduce hole pressure errors). Thus, such right angle measurement is not preferred.

FIGS. 10 and 11 show an alternate embodiment of the plunger pressure transducer assembly 73 which includes an optical pressure sensing arrangement. As shown, the optical sensing arrangement includes an input optical fiber 75, diaphragm 78 and an output optical fiber 76. The diaphragm 78 deflects in response to pressure by the polymer melt 60 within the reservoir 62. The diaphragm includes a moveable reflector 80 attached thereto and a fixed reflector 82. When the diaphragm 78 deflects in response to pressure, the moveable reflector 80 moves therewith. One skilled in the art will appreciate that the optical pressure sensing arrangement plunger assembly 73, while shown in FIGS. 10 and 11 for use in the apparatus of FIG. 9, can be used also with the apparatus shown in FIG. 3.

The optical sensing mechanism operates as follows. Input light from an input source 84 is coupled into an input optical fiber 75, reflects off of movable reflector 80, then reflects off of fixed reflector 82 and is coupled into an output optical fiber 76. The light coupled into output optical fiber 76 is detected by photodetector 86. The amount of light coupled into an output optical fiber varies with the position of the movable reflector 80. Because the movable reflector moves in response to pressure in the liquid melt 60, the optical sensing mechanism determines, from the amount of light detected at the photodetector 86, the amount of pressure of the liquid melt 60. Photodetector 88 receives a small predetermined reflected portion of the input light generated by input light source 84 to monitor the amount of input light generated. A feedback arrangement (not shown) is connected from photodetector 88 to input light source 84 to control input light source 84. In that manner, a maximum constant amount of input light is coupled into an input optical fiber 74 thereby optimizing the accuracy and stability of the optical pressure sensing arrangement. Input light source 84 can be an LED. The optical sensing mechanism is described in U.S. patent application Ser. No. 07/907,331 entitled "OPTICAL PRESSURE TRANSDUCER" filed Jul. 1, 1992, which is herein incorporated by reference.

It is to be appreciated, that the use of the plunger transducer assembly and instrumented piston, as opposed to the prior art force based plunger, eliminated friction errors and reduces leakage errors without influencing the measured pressure. Additionally, the alternate embodiment optical pressure measuring apparatus produces a highly accurate pressure measurement.

It is to be appreciated that the preferred embodiment of the present invention utilized a plunger pressure transducer assembly in a force based type capillary rheometer which allows for the determination of melted polymer material properties without certain errors associated with the force based type capillary rheometer, but the plunger pressure transducer assembly is not limited to use in a force based type capillary rheometer.

Having now described a limited number of embodiments of the invention, it should not be apparent to those skilled in the art that numerous embodiments and modifications thereof are contemplated as falling within the scope of the present invention as defined by the appended claims.

What is claimed is:

1. A capillary rheometer apparatus for characterizing a polymer melt's pressure-volume-temperature relationship, comprising:
   a housing;
   a plunger;
   the housing having a reservoir for receiving the plunger and the polymer melt;
   a plug for blocking flow of the melt out of the reservoir;
   a driving mechanism for driving the plunger longitudinally within the reservoir;
   the plunger having a liquid-filled capillary passage extending therein from one end of the plunger;
   a coupler at the one end of the plunger defining within the plunger a chamber in communication with the capillary passage and for sensing melt pressure in the reservoir and transmitting the pressure to the liquid-fill; and
   a pressure sensing mechanism, at a second end of and coupled to the capillary passage, responsive to pressure exerted by the liquid fill, for providing an indication of sensed pressure.

2. A capillary rheometer as claimed in claim 1 further including a temperature controller, coupled to the housing, for controlling the temperature of the housing.

3. A capillary rheometer as claimed in claim 1 further including a position detecting sensor, coupled to the plunger, for detecting longitudinal movement of the plunger.

4. A capillary rheometer as claimed in claim 1 further including insulation material surrounding said housing for insulating the housing.

5. A capillary rheometer as claimed in claim 1, wherein the plug includes a temperature sensor for sensing a temperature of the polymer melt.

6. A capillary rheometer as claimed in claim 5, wherein the temperature sensor includes a probe inserted into an aperture in the reservoir.

7. A capillary rheometer apparatus for characterizing a polymer melt's pressure-volume-temperature relationship, comprising:
   a housing;
   a plunger having a piston at one end thereof;

the housing having a reservoir for receiving the piston and the polymer melt;

means for blocking flow of the melt out of the reservoir;

a driving mechanism for driving the plunger and piston longitudinally within the reservoir;

means, coupled to the plunger, for determining pressure of the melt;

means, coupled to the reservoir, for determining the temperature of the melt; and means, coupled to the plunger, for sensing a longitudinal position of the plunger.

8. A capillary rheometer as claimed in claim 7 wherein the means coupled to the plunger includes an instrumented piston attached to the one end of the plunger.

9. A capillary rheometer as claimed in claim 8 wherein the instrumented piston includes a seal for sealing space between the piston and reservoir.

10. A capillary rheometer as claimed in claim 7 further including means, coupled to the housing, for controlling the temperature of the housing.

11. A capillary rheometer as claimed in claim 10 wherein the means for blocking flow includes a plug disposed within an opening in the housing at one side of the reservoir.

12. A capillary rheometer as claimed in claim 11 wherein the piston includes a seal thereon for sealing space between the piston and reservoir.

13. A capillary rheometer as claimed in claim 7 wherein the means for determining pressure of the melt includes an optical pressure sensing mechanism.

14. A capillary rheometer as claimed in claim 7 wherein the means for determining pressure of the melt includes the piston attached to the plunger and a liquid-filled capillary passage extending within the plunger.

15. A capillary rheometer apparatus for characterizing a polymer melt's pressure-volume-temperature relationship, comprising:
 a housing;
 a plunger;
 the housing having a reservoir for receiving the plunger and the polymer melt;
 a plug for blocking flow of the melt out of the reservoir;
 a driving mechanism for driving the plunger longitudinally within the reservoir to move one end of the plunger in contact with the melt;
 a diaphragm, coupled to one end of said plunger, for deflecting in response to melt pressure in the reservoir; and
 means, responsive to diaphragm deflection, for determining pressure of the melt.

16. A capillary rheometer as claimed in claim 15 wherein the means for determining melt pressure includes an optical sensing mechanism.

17. A capillary rheometer as claimed in claim 16 further including:
 means, coupled to the reservoir, for determining the temperature of the melt; and
 means, coupled to the plunger, for indicating longitudinal movement of the plunger.

18. A capillary rheometer as claimed in claim 16 wherein the optical sensing mechanism includes an input optical fiber, an output optical fiber, a fixed reflector, a movable reflector coupled to the diaphragm, a light source, and a light level detector.

19. A capillary rheometer as claimed in claim 15 wherein the means for determining melt pressure includes the diaphragm at the one end of the plunger and a liquid-filled capillary passage extending within the plunger.

20. A capillary rheometer as claimed in claim 19 further including:
 means, coupled to the reservoir, for determining the temperature of the melt; and
 means, coupled to the plunger, for indicating longitudinal movement of the plunger.

21. A method for characterizing a polymer melt's pressure-volume-temperature relationship, comprising:
 introducing the polymer material into a reservoir contained within a housing;
 heating the housing to melt the polymer;
 applying pressure to the polymer with a plunging apparatus introduced into an aperture of the reservoir;
 measuring a pressure of the polymer melt with a pressure sensing apparatus coupled to the plunger; and
 measuring a temperature of the polymer melt with a probe introduced into the reservoir.

22. The method of characterizing a polymer melt at claimed in claim 21, further comprising the steps of:
 repeating the steps of applying pressure, measuring the pressure, and measuring the temperature for a number of pressures applied to the polymer melt.

* * * * *